United States Patent
Parmar et al.

(10) Patent No.: US 11,667,614 B2
(45) Date of Patent: Jun. 6, 2023

(54) PROCESS FOR THE PREPARATION OF HIGHLY PURE SALCAPROZIC ACID AND PHARMACEUTICALLY ACCEPTABLE SALTS THEREOF

(71) Applicant: Navinta III Inc, Boca Raton, FL (US)

(72) Inventors: Pankaj Vasudev Parmar, Vadodara (IN); Raja Jeyakumar John Muthiah, Vadodara (IN); Vikas Kantilal Chauhan, Vadodara (IN); Jagdish Kanjibhai Solanki, Vadodara (IN)

(73) Assignee: Navinta III Inc., Boca Raton, FL (US)

( * ) Notice: Subject to any disclaimer, the term of this patent is extended or adjusted under 35 U.S.C. 154(b) by 0 days.

(21) Appl. No.: 17/720,007

(22) Filed: Apr. 13, 2022

(65) Prior Publication Data

US 2022/0332688 A1    Oct. 20, 2022

Related U.S. Application Data

(60) Provisional application No. 63/176,029, filed on Apr. 16, 2021.

(51) Int. Cl.
   *C07D 265/26*    (2006.01)
(52) U.S. Cl.
   CPC ................. *C07D 265/26* (2013.01)
(58) Field of Classification Search
   CPC .................................... C07D 265/26
   See application file for complete search history.

(56) References Cited

U.S. PATENT DOCUMENTS

| | | | |
|---|---|---|---|
| 3,681,482 A | * | 8/1972 | Patel .................. C07F 9/12 558/150 |
| 5,650,386 A | | 7/1997 | Leone-Bay et al. |
| 5,866,536 A | | 2/1999 | Leone-Bay et al. |
| 9,278,123 B2 | | 3/2016 | Sauerberg et al. |

FOREIGN PATENT DOCUMENTS

| | | | | |
|---|---|---|---|---|
| CN | 104974060 A | * | 10/2015 | |
| CN | 108689876 A | * | 10/2018 | ........... C07C 231/12 |
| CN | 111978193 A | * | 11/2020 | ........... C07C 231/02 |
| CN | 112661662 A | * | 4/2021 | |
| WO | 0059863 A1 | | 10/2000 | |
| WO | 0192206 A1 | | 12/2001 | |
| WO | 2008028859 A1 | | 3/2008 | |
| WO | WO-2022162132 A1 | * | 8/2022 | |

OTHER PUBLICATIONS

International Search Report for Application # PCT/US2022/024963 dated Jul. 12, 2022.

* cited by examiner

*Primary Examiner* — Daniel R Carcanague
(74) *Attorney, Agent, or Firm* — St. Onge Steward Johnston & Reens LLC

(57) ABSTRACT

Processes that use novel reagents for the removal of colored impurity during the preparation of Salcaprozic Acid and pharmaceutically acceptable salts thereof. The processes include hydrolysis of 8-(2,4-dioxo-1,3-benzoxazin-3-yl)octanoic acid ethyl ester in the presence of or by contacting it with benzotriazole, hydrazine and/or sodium borohydride.

20 Claims, 1 Drawing Sheet

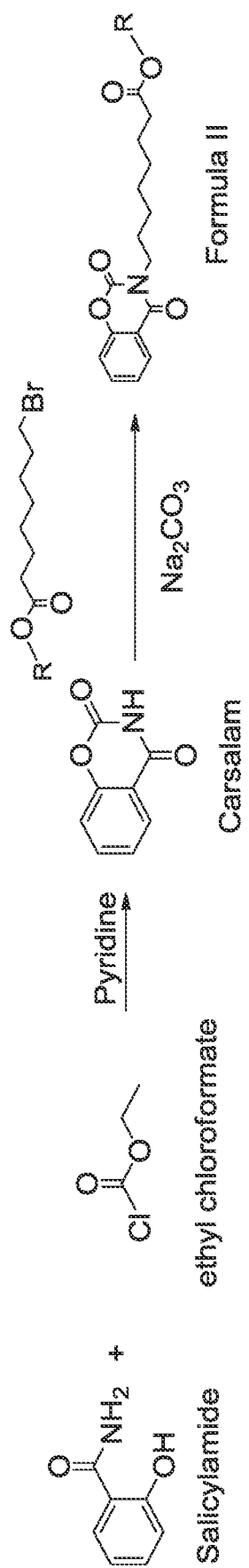

PROCESS FOR THE PREPARATION OF HIGHLY PURE SALCAPROZIC ACID AND PHARMACEUTICALLY ACCEPTABLE SALTS THEREOF

FIELD OF THE INVENTION

The present invention relates to a process for the preparation of Salcaprozic Acid and pharmaceutically acceptable salts thereof. The present invention also relates to a process for the purification of Salcaprozic Acid. More specifically, the process of the present invention comprises use of novel reagents for preventing the formation of colored impurity in Salcaprozic Acid and pharmaceutically acceptable salts thereof.

BACKGROUND OF THE INVENTION

Many current commercial formulations containing peptides as active agents are delivered by a non-oral route, which is not convenient for patients. Use of N-[-8-(2-hydroxybenzoyl)amino] caprylic acid as an excipient which operates as a permeation enhancer or delivery agent is known to allow delivery of some peptides in an oral dosage form. It is believed that N-[-8-(2-hydroxybenzoyl)amino] caprylic acid temporarily alters the intestinal barrier to improve absorption of the peptide. N-[-8-(2-hydroxybenzoyl)amino] caprylic acid is also known as Salcaprozic Acid and is represented by formula A:

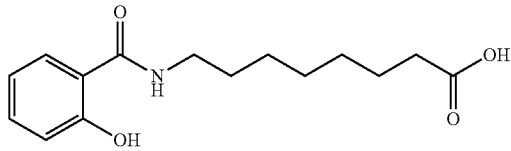

formula A

U.S. Pat. No. 5,650,386 discloses N-[-8-(2-hydroxybenzoyl)amino] caprylic acid or salts thereof, which can facilitate the delivery of various active agents with low oral bioavailability such as heparin, peptides, parathyroid hormone, bisphosphonates, vitamin B12.

U.S. Pat. No. 5,866,536 also discloses use of salts of N-[-8-(2-hydroxybenzoyl)amino] caprylic acid for delivering active agents such as heparin and calcitonin for oral administration.

U.S. Pat. No. 9,278,123 (WO 2012/080471) discloses use of Salcaprozic Acid salts as a delivery agent in solid oral compositions of GLP-1 peptide. The PCT application discloses oral composition of Semaglutide with a monosodium salt of Salcaprozic Acid. In 2019, an oral tablet of Semaglutide in accordance with this patent and commercialized by Novo Nordisk was approved by the FDA.

General processes for the preparation of Salcaprozic Acid and its salts have also been described in the literature.

U.S. Pat. No. 5,650,386 teaches reaction of 0-acetylsalicyl chloride with 8-aminooctanoic acid and 2-azacyclononanone respectively to yield Salcaprozic Acid.

A process according to WO 2000/59863 comprises coupling of 1,3-Benzoxazine 2,4-Dione (Carsalam) with ethyl-8-bromooctanoate followed by hydrolytic ring opening of the corresponding ethyl ester intermediate to yield Salcaprozic Acid.

WO 2001/092206 and WO 2008/028859 disclose processes for the preparation of N-[-8-(2-hydroxybenzoyl)amino] caprylic acid and a sodium salt thereof. Apart from the sodium salt, both applications disclose general base addition salts of N-[-8-(2-hydroxybenzoyl)amino] caprylic acid, such as alkali-metal salts (Na, K, Li), alkaline-earth metal salts (Mg, Ca, Ba), ammonium salts, basic amino acid salts (lysine, arginine), organic amines (dimethylamine, pyridine) and quaternary ammonium hydroxide salts (tetramethylammonium hydroxide).

In most of instances, the prior-art processes impart a pink color to the final Salcaprozic Acid or pharmaceutically acceptable salt thereof. WO 2008/028859 hypothesized that trace metals and/or oxygen are responsible for the formation of the pink color impurity, which is carried forward during salt formation and remains unaltered even after a number of purifications. The application discloses use of metal complexing agents like Ethylenediamine tetraacetic acid (EDTA), and reducing agents such as ascorbic acid (1%), Sodium bisulfite ($NaHSO_3$) (1%) and Triphenylphosphine ($PPh_3$) (0.1%) for removal of the unknown pink colored impurity from Salcaprozic Acid.

There is a desire to have alternative processes for preparing Salcaprozic Acid and its pharmaceutically acceptable salts that do not produce a pink color/impurity in the final product.

We have found that certain novel reagents can also be used for the removal of colored impurity/impurities from Salcaprozic Acid, and thus incorporation thereof in the process yields desired Salcaprozic Acid and pharmaceutically acceptable salts thereof without colored impurity.

SUMMARY OF THE INVENTION

The present disclosure provides a processes for the preparation of Salcaprozic Acid and pharmaceutically acceptable salts thereof, which are free from colored impurity. The processes comprise use of novel reagents for removal of colored impurity.

In a first aspect, the present disclosure provides a process for the preparation of Salcaprozic Acid or a pharmaceutically acceptable salt thereof, comprising hydrolyzing a compound of formula II:

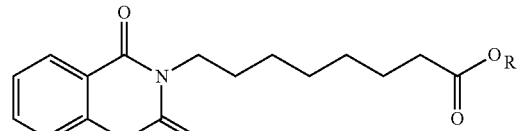

formula II wherein, R is straight or branched chain alkyl
in the presence of benzotriazole, hydrazine, Sodium borohydride or mixture thereof; and isolating Salcaprozic Acid, which is free from colored impurity.

Preferably, the compound of formula II is 8-(2,4-dioxo-1,3-benzoxazin-3-yl)octanoic acid ethyl ester.

In certain embodiments, the compound of formula II is prepared from 1,3-Benzoxazine-2,4-dione. In certain of those embodiments, about 1% to about 5% by weight of the benzotriazole, hydrazine, sodium borohydride or mixture thereof is used relative to weight of the 1,3-Benzoxazine-2,4-dione.

In some embodiments, the step of hydrolyzing occurs at ambient temperature.

In certain embodiments, the step of hydrolyzing comprises adding aqueous metal hydroxide and stirring at an elevated temperature up to about 95° C. In some of those embodiments, the process comprises cooling to 0-5° C. followed by adjusting pH to about 9 to about 10. In certain of those embodiments, the process further comprises washing the pH adjusted solution with an organic solvent followed by discarding the organic washing solvent. In some of those embodiments, the step of isolating comprises lowering pH of the washed solution to obtain a wet solid Salcaprozic Acid.

In some embodiments, the process further comprises filtering and washing the isolated Salcaprozic Acid with a mixture of acetone and water.

In certain embodiments, the process further comprises contacting Salcaprozic Acid, which his free from colored impurity, with an organic or inorganic base in an organic solvent, water, or a mixture thereof to obtain a salt of Salcaprozic Acid. In some of those embodiments, absorbance at 400 nm of a 1% solution of the salt of Salcaprozic Acid is less than 0.03 and/or transmission at 600 nm of a 1% solution of the salt of Salcaprozic Acid is greater than 95%.

Also described is a process for removing a colored impurity from a Salcaprozic Acid salt comprising treating a solution of the salt with benzotriazole, hydrazine, sodium borohydride or a mixture thereof. Absorbance at 400 nm of a 1% solution of the treated salt is less than 0.03.

In another aspect, a process for the preparation of Salcaprozic Acid or a pharmaceutically acceptable salt thereof, comprises preparing 8-(2,4-dioxo-1,3-benzoxazin-3-yl)octanoic acid ethyl ester using 1,3-Benzoxazine-2,4-dione;

contacting the 8-(2,4-dioxo-1,3-benzoxazin-3-yl)octanoic acid ethyl ester with about 1% to about 5% by weight of benzotriazole, hydrazine, sodium borohydride or mixture thereof relative to the amount of 1,3-Benzoxazine-2,4-dione, adding aqueous metal hydroxide and stirring at an elevated temperature up to about 95° C.;

cooling to 0-5° C. followed by adjusting pH to about 9 to about 10;

washing the pH adjusted solution with an organic solvent followed by discarding the organic washing solvent; and lowering pH of the washed solution to isolate a wet solid Salcaprozic Acid.

In some embodiments, the step of contacting occurs at ambient temperature.

In certain embodiments, the process further comprises filtering and washing the wet solid Salcaprozic Acid with a mixture of acetone and water to obtain purified Salcaprozic Acid.

Advantageously, the processes disclosed herein produce Salcaprozic Acid that is free of or substantially free of colored impurity. That is, the Salcaprozic Acid has no detectable levels of trace metals and/or oxygen generated impurities that impart a pink color to the product. The Salcaprozic Acid produced according to this disclosure is considered to be colorless upon visual inspection or against a standard colorless solution. Salcaprozic Acid salts produced in accordance with this disclosure are white solids.

In certain preferred embodiments, an amount of any single impurity in the purified Salcaprozic Acid according to the processes described is less than 0.1%. Moreover, a 1% solution of a sodium salt of the Salcaprozic Acid made in accordance with this disclosure has absorbance at 400 nm of less than 0.02 or transmission at 600 nm of greater than 99%.

DESCRIPTION OF THE DRAWINGS

FIG. 1 shows a reaction scheme for preparation of a compound of formula II.

DETAILED DESCRIPTION OF THE INVENTION

A wide range of reagents have been studied in order to achieve Salcaprozic Acid or a pharmaceutically acceptable salt thereof, which is essentially free from colored impurity. We have found three such novel reagents, which remove colored impurity and yield colorless Salcaprozic Acid or a pharmaceutically acceptable salt thereof as a white solid. Benzotriazole, hydrazine and sodium borohydride are such novel reagents of the present invention for the removal of colored impurity during the preparation of Salcaprozic Acid or pharmaceutically acceptable salts thereof.

The term "colored impurity" as used herein, refers to one impurity or more than one impurity or impurities that imparts a color to a substance, which may exist in amounts as low as a few parts per billion and still affect the color of substance. The "colored impurity" may be detected by visual inspection of a solid sample or its solution by reference or comparison to a standard colorless solid or solution.

The term "ambient temperature" means a temperature ranging from about 15° C. to 40° C., preferably to a temperature ranging from about 20° C. to 35° C.

The term "contacting" includes mixing, adding, slurring, stirring or a combination thereof. The term "contacting", as used herein for the purpose of reaction, is wherein one or more reagent(s) are mixed or added with each other, in the presence or absence of solvent(s) or an aqueous medium, in any sequence as a slurry or an insoluble solid mixture or stirred as a clear solution.

The term "about" is to be construed as modifying a term or value such that it is not an absolute. Such terms will be defined by the circumstances. This includes, at the very least, the degree of expected experimental error, technique error and instrument error for a given technique used to measure a value.

The term "comprising" and "comprises" mean the elements or steps as recited, or their equivalents in structure or function, plus any other element or elements which are not recited.

The terms "having" and "including" are also to be construed as open ended.

All ranges recited herein include the endpoints, including those that recite a range between two values. Whether so indicated or not, all values recited herein are approximate as defined by the circumstances, including the degree of expected experimental variation, technique variation, and instrument variation for a given technique used to measure a value.

The term "pharmaceutically acceptable salt" is to be construed as conventional base-addition salts that retain or improve the effectiveness or properties of Salcaprozic Acid and are formed from suitable non-toxic bases. The carboxylic acid (—COOH) and phenolic hydroxyl (—OH) moieties of Salcaprozic Acid may take part in converting to base addition salt. Sample base addition salts include, but are not limited to, inorganic or organic salts, for example alkali-metal salts such as sodium, potassium and lithium; alkaline-earth metal salts such as magnesium, calcium or barium;

ammonium salts; basic amino acids, such as lysine or arginine; and organic amines, such as dimethylamine, triethylamine or pyridine. Based on the atom valances, the alkali-metal and alkaline-earth metal salts include, but not limited to, hemi-, mono-, di- and other multi-valent salts, such as, mono-sodium, di-sodium, mono-potassium, di-potassium, hemi-calcium, hemi-magnesium.

A process for the preparation of Salcaprozic Acid or a pharmaceutically acceptable salt thereof, comprises hydrolyzing a compound of formula II:

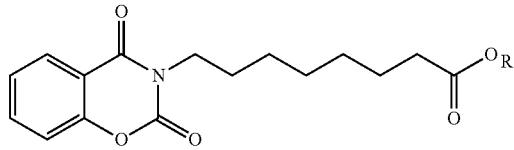

formula II wherein, R is straight or branched chain alkyl in the presence of one or more novel reagents. The reagents for hydrolysis are selected from benzotriazole, hydrazine, and sodium borohydride or a mixture thereof.

The compound of formula II may be prepared according to methods known in art, or preferably by the process of FIG. 1. Reaction between Salicylamide and ethyl chloroformate is carried out in pyridine and methanol to obtain 1,3-Benzoxazine-2,4-dione (Carsalam). Coupling of 1,3-Benzoxazine-2,4-dione with an alkyl ester of 8-bromoctanoic acid is carried out in the presence of sodium carbonate as base and dimethyl acetamide as solvent to yield compound of formula II. Further, the compound of formula II may be isolated and optionally dried. Preferably, the compound of formula II is hydrolyzed without drying, as wet solid, to obtain Salcaprozic Acid.

In certain embodiments, the process includes contacting the hydrolyzed reaction mixture with one or more of the novel reagents.

The novel reagents are used in quantities sufficient to remove colored impurity from the Salcaprozic Acid, preferably from 0.1% to 10% w/w, more preferably from about 1% to about 5% by weight relative to amount of 1,3-Benzoxazine-2,4-dione.

Hydrolysis of the compound of formula II may be carried out in acidic or basic media; preferably, it is a base mediated hydrolysis, wherein the base is metal hydroxide selected from sodium, potassium, lithium or calcium hydroxides.

The hydrolysis may be carried out in an aqueous media at a temperature ranging from ambient temperature to reflux temperature and for the time sufficient to complete the hydrolysis of the compound of formula II.

In one preferred embodiment, the hydrolyzed reaction mixture comprises base addition salt of Salcaprozic Acid.

The hydrolyzed reaction mixture is acidified using aqueous hydrochloric acid to yield Salcaprozic Acid that is free from colored impurity. Alternatively, the hydrolyzed reaction mixture is first adjusted to an intermediate pH between 9 to 10 using aqueous hydrochloric acid followed by washing with an organic solvent selected from toluene, diisopropyl ether, dichloromethane or ethyl acetate. An obtained aqueous layer is further acidified using aqueous hydrochloric acid to yield Salcaprozic Acid that is free of colored impurity.

Before acidification of the hydrolyzed reaction mixture or an aqueous layer obtained after organic solvent washing, the hydrolyzed reaction mixture may be subjected to re-treatment with the novel reagent(s) to ensure complete removal of colored impurity.

A process of the present aspect may further comprise purification of Salcaprozic Acid in acetone:water to ensure complete removal of any other impurity.

In some embodiments, the purification includes suspending in acetone and stirring for about 5 hours at ambient temperature followed by addition of water at ambient temperature. The reaction mixture is filtered and washed with a mixture of acetone:water followed by drying to yield Salcaprozic Acid that is free from colored impurity as well as other process related impurities.

The process may further comprise conversion of colorless Salcaprozic Acid to its pharmaceutically acceptable salt(s). The pharmaceutically acceptable salts comprise but are not limited to sodium, potassium, calcium, magnesium, ammonium or organic amine addition salts. Preferably, Salcaprozic Acid is converted to corresponding sodium and potassium salts; more preferably, mono-sodium and mono-potassium.

A process for the conversion of Salcaprozic Acid to a pharmaceutically acceptable salt thereof comprises contacting Salcaprozic Acid with an organic or inorganic base in an organic solvent, water or a mixture thereof; and isolating a pharmaceutically acceptable salt of Salcaprozic Acid.

Alternatively, a process for the conversion of Salcaprozic Acid to a pharmaceutically acceptable salt thereof comprises contacting Salcaprozic Acid with an organic or inorganic base in an organic solvent, water or a mixture thereof to obtain a first salt of Salcaprozic Acid; and converting the first salt to a desired pharmaceutically acceptable salt of Salcaprozic Acid.

The selection of an organic or inorganic base is based on which pharmaceutically acceptable salt is desired. Preferably, an organic or an inorganic bases may be selected from sodium hydroxide, sodium methoxide, sodium ethoxide, potassium hydroxide, potassium methoxide, potassium ethoxide, calcium hydroxide, magnesium hydroxide or ammonium hydroxide; and organic bases may be selected from dimethylamine, triethylamine or pyridine. Preferably, the base is sodium hydroxide or potassium hydroxide and in the amount sufficient to obtain mono-sodium and mono-potassium salt, respectively.

The solvent is selected from methanol, ethanol or a mixture thereof. The pharmaceutically acceptable salt of Salcaprozic Acid is isolated by addition of a non-polar solvent, which acts as an anti-solvent. A non-polar solvent is preferably selected from heptane, diisopropylether, methyl tert-butyl ether, acetonitrile or a mixture thereof.

The processes of present invention utilizing benzotriazole, hydrazine and sodium borohydride yield better results as compared to prior art processes. If any of the contemplated reagents is not used in the process, it leads to Salcaprozic Acid with greater absorbance. Accordingly, the processes described herein are able to produce Salcaprozic Acid and salts thereof having absorbance at 400 nm of less than 0.03, preferably less than 0.02, most preferably about 0.01 or less, and a transmission of greater than 95%, more preferably greater than 98%, most preferably about 99% or greater, while maintaining high purity (e.g., greater than 99%).

EXAMPLES

Example 1: Preparation of Salcaprozic Acid Using 2% Benzotriazole Relative to 1,3-Benzoxazine 2,4-Dione

Step 1: Preparation of 8-(2,4-dioxo-1,3-benzoxazin-3-yl)octanoic acid ethyl ester (Formula II)

1,3-Benzoxazine-2,4-dione (200 g) was added to dimethylacetamide (900 mL) followed by addition of ethyl 8-bromo octanoate (292.5 g) in dimethylacetamide (100 mL). The reaction mixture was allowed to stir for 30 minutes at 45-50° C. and sodium carbonate (147.5 g) was added. The temperature was raised to 75-80° C. and maintained until the reaction was complete. The reaction mixture was cooled to ambient temperature and water (1200 mL) was charged. The solid was filtered and washed with water (400 mL). The wet solid was subjected to slurry wash with water (1000 mL) for 1 hour followed by filtration and washing with water (400 mL) to obtain 612.5 g of wet 8-(2,4-dioxo-1,3-benzoxazin-3-yl)octanoic acid ethyl ester.

Step 2: Hydrolysis of 8-(2,4-dioxo-1,3-benzoxazin-3-yl)octanoic acid ethyl ester (2% benzotriazole Relative to 1,3-Benzoxazine 2,4-Dione)

Method A: Water (425 mL) was charged to 8-(2,4-dioxo-1,3-benzoxazin-3-yl)octanoic acid ethyl ester prepared by the same process as in Step 1 (520.66 g wet solid was obtained from 170 gm 1,3-Benzoxazine 2,4-Dione) at ambient temperature followed by addition of benzotriazole (3.4 g) and stirred for 30 minutes. The reaction mixture was charged with aqueous sodium hydroxide solution (178.5 g NaOH in 714 mL water) and stirred at 95° C. for 120 minutes. The reaction mixture was cooled to 0-5° C. followed by pH adjustment between 9 and 10 using concentrated HCl (153 mL). The reaction mixture was brought to ambient temperature and aqueous layer was washed using toluene (850 mL×3), wherein toluene layer was discarded. The aqueous layer (1966 g) was further divided in two equal parts (983 g each) followed by further treatments according to Method A-1 or Method A-2.

Step 3: Isolation of Salcaprozic Acid

Method A-1: One part of the aqueous layer (983 g) as obtained above was charged with sodium borohydride (1.7 g) and stirred for an hour at ambient temperature. The reaction mixture was added to pre-cooled aqueous HCl solution (179 mL conc. HCl in 510 mL water) and stirred for 30 minutes at 0-5° C. The solid was filtered, washed with water (170 mL) and slurry washed with water (425 mL) followed by filtration and washing with water (595 mL). The wet Salcaprozic Acid solid, free from colored impurity was further purified as described in Step 4 below.

Method A-2: Second part of the aqueous layer (983 g) as obtained above was added to pre-cooled aqueous HCl solution (179 mL conc. HCl in 510 mL water) and stirred for 30 minutes at 0-5° C. The solid was filtered, washed with water (170 mL) and slurry washed with water (425 mL) followed by filtration and washing with water (595 mL). The wet Salcaprozic Acid, free from colored impurity was further purified as described in Step 4 below.

Step 4: Purification of Salcaprozic Acid

The wet Salcaprozic Acid obtained from Method A-1 was charged with acetone (425 mL) and stirred for about 5 hours at ambient temperature. The reaction mixture was then diluted with water (850 mL) and further stirred for about an hour at ambient temperature. The solid was filtered, washed with a mixture of acetone:water (85 mL:170 mL) and dried for 2 hours. The wet cake was unloaded and dried under vacuum at 50-55° C. for 15 hours to obtain pure Salcaprozic Acid (109 g).

The wet Salcaprozic Acid obtained from Method A-2 was charged with acetone (425 mL) and stirred for about 5 hours at ambient temperature. The reaction mixture was then charged water (850 mL) and further stirred for about an hour at ambient temperature. The solid was filtered, washed with a mixture of acetone:water (85 mL:170 mL) and suck-dried for 2 hours. The wet cake was unloaded and dried under vacuum at 50-55° C. for 15 hours to obtain pure Salcaprozic Acid (107 g).

Example 2: Preparation of Salcaprozic Acid

Step 1: Preparation of 8-(2,4-dioxo-1,3-benzoxazin-3-yl)octanoic acid ethyl ester (Formula II)

1,3-Benzoxazine-2,4-dione (500 g) was added to dimethylacetamide (2250 mL) followed by addition of ethyl 8-bromo octanoate (731 g) in dimethylacetamide (250 mL). The reaction mixture was allowed to stir for 30 minutes at 45-50° C. and was added sodium carbonate (367.5 g). The temperature was raised to 75-80° C. and maintained until the reaction was completed. The reaction mixture was cooled to ambient temperature and water (3000 mL) was charged. The solid was filtered and washed with water (1000 mL). The wet solid was subjected to slurry wash with water (2500 mL) for 1 hour followed by filtration and washing with water (1000 mL). The mixture was filtered to obtain 1486 g of wet solid of 8-(2,4-dioxo-1,3-benzoxazin-3-yl)octanoic acid ethyl ester (Formula II).

Step 2: Hydrolysis

Wet solids of 8-(2,4-dioxo-1,3-benzoxazin-3-yl)octanoic acid ethyl ester obtained by the process of Step 1 were further hydrolyzed to Salcaprozic Acid by Method B, Method C, Method D, Method E, Method F & Method G as described below.

Method B: (5% benzotriazole Relative to 1,3-Benzoxazine 2,4-Dione):

Water (50 mL) was charged to 8-(2,4-dioxo-1,3-benzoxazin-3-yl)octanoic acid ethyl ester (29.72 g wet solid was obtained from 10 gm of 1,3-Benzoxazine-2,4-dione) at ambient temperature followed by addition of benzotriazole (0.5 g) and stirred for 30 minutes. The aqueous sodium hydroxide solution (10.5 g NaOH in 42 mL water) was charged into reaction mass and stirred at 95° C. for 120 minutes. The reaction mixture was cooled to 0-5° C. followed by pH adjustment between 9 and 10 using concentrated HCl (7.5 mL). The reaction mixture was brought to ambient temperature and aqueous layer was washed using toluene (50 mL×3), wherein toluene layer was discarded. The reaction mixture was charged into pre-cooled mixture of HCl (22.5 mL conc. HCl in 60 mL water) and stirred for 30 minutes at 0-5° C. The solid was filtered, washed with water (20 mL). The wet solid was subjected to slurry wash with water (50 mL) for 1 hour followed by filtration and washing with water (70 mL) followed by suck-drying. The wet Salcaprozic Acid, free from colored impurity was further purified as described in Step 3 below.

Method C: (1% benzotriazole Relative to 1,3-Benzoxazine 2,4-Dione)

Water (125 mL) was charged to 8-(2,4-dioxo-1,3-benzoxazin-3-yl)octanoic acid ethyl ester (74.3 g solid was obtained from 25 g of 1,3-Benzoxazine-2,4-dione) at ambient temperature followed by addition of benzotriazole (0.25 g) and stirred for 30 minutes. The aqueous sodium hydroxide solution (26.25 g NaOH in 105 mL water) charged into reaction mass and stirred at 95° C. for 120 minutes. The reaction mixture was cooled to 0-5° C. followed by pH adjustment between 9 and 10 using concentrated HCl (19 mL). The reaction mixture was brought to ambient temperature and aqueous layer was washed using toluene (125 mL×3), wherein toluene layer was discarded.

The reaction mixture was charged into pre-cooled mixture of HCl (56 mL conc. HCl in 150 mL water) and stirred for 30 minutes at 0-5° C. The solid was filtered, washed with water (50 mL). The wet solid was subjected to slurry wash with water (125 mL) for 1 hour followed by filtration and washing with water (175 mL) followed by suck-drying. The wet solid Salcaprozic Acid, free from colored impurity was further purified as described in Step 3 below Method D: (1% hydrazine Relative to 1,3-Benzoxazine 2,4-Dione)

Water (50 mL) was charged to 8-(2,4-dioxo-1,3-benzoxazin-3-yl)octanoic acid ethyl ester (29.72 g wet solid was obtained from 10 g of 1,3-Benzoxazine-2,4-dione) at ambient temperature followed by addition of hydrazine (0.1 g) and stirred for 30 minutes. An aqueous sodium hydroxide solution (10.5 g NaOH in 42 mL water) was charged into reaction mass and stirred at 95° C. for 120 minutes. The reaction mixture was cooled to 0-5° C. followed by pH adjustment between 9 and 10 using concentrated HCl (7.5 mL). The reaction mixture was brought to ambient temperature and aqueous layer was washed using toluene (50 mL×3), wherein toluene layer was discarded. The reaction mixture was charged into pre-cooled mixture of HCl (22.5 mL conc. HCl in 60 mL water) and stirred for 30 minutes at 0-5° C. The solid was filtered, washed with water (20 mL). The wet solid was subjected to slurry wash with water (50 mL) for 1 hour followed by filtration and washing with water (70 mL) followed by suck-drying. The wet Salcaprozic Acid solid, free from colored impurity was further purified as described in Step 3 below Method E: (2% hydrazine Relative to 1,3-Benzoxazine 2,4-Dione)

Water (50 mL) was charged to 8-(2,4-dioxo-1,3-benzoxazin-3-yl)octanoic acid ethyl ester (29.72 g wet solid was obtained from 10 g of 1,3-Benzoxazine-2,4-dione) at ambient temperature followed by addition of hydrazine (0.2 g) and stirred for 30 minutes. The aqueous sodium hydroxide solution (178.5 g NaOH in 714 mL water) charged into reaction mass and stirred at 95° C. for 120 minutes. The reaction mixture was cooled to 0-5° C. followed by pH adjustment between 9 and 10 using concentrated HCl (7.5 mL). The reaction mixture was brought to ambient temperature and aqueous layer was washed using toluene (50 mL×3), wherein toluene layer was discarded. The reaction mixture was charged into pre-cooled mixture of HCl (22.5 mL conc. HCl in 60 mL water) and stirred for 30 minutes at 0-5° C. The solid was filtered, washed with water (20 mL). The wet solid was subjected to slurry wash with water (50 mL) for 1 hour followed by filtration and washing with water (70 mL) followed by suck-drying. The wet Salcaprozic Acid solid, free from colored impurity was further purified as described in Step 3 below Method F: (5% hydrazine Relative to 1,3-Benzoxazine 2,4-Dione)

Water (50 mL) was charged to 8-(2,4-dioxo-1,3-benzoxazin-3-yl)octanoic acid ethyl ester (29.72 g wet solid was obtained from 10 g of 1,3-Benzoxazine-2,4-dione) at ambient temperature followed by addition of hydrazine (0.5 g) and stirred for 30 minutes. The reaction mixture was charged with aqueous sodium hydroxide solution (10.5 g NaOH in 42 mL water) and stirred at 95° C. for 120 minutes. The reaction mixture was cooled to 0-5° C. followed by pH adjustment between 9 and 10 using concentrated HCl (7.5 mL). The reaction mixture was brought to ambient temperature and aqueous layer was washed using toluene (50 mL×3), wherein toluene layer was discarded. The reaction mixture was charged to pre-cooled mixture of HCl (22.5 mL conc. HCl in 60 mL water) and stirred for 30 minutes at 0-5° C. The solid was filtered, washed with water (20 mL). The wet solid was subjected to slurry wash with water (50 mL) for 1 hour followed by filtration and washing with water (70 mL) followed by suck-drying. The wet Salcaprozic Acid solid, free from colored impurity was further purified as described in Step 3 below Method G: (Total 4% Sodium Borohydride Relative to 1,3-Benzoxazine 2,4-Dione)

Water (50 mL) was charged to 8-(2,4-dioxo-1,3-benzoxazin-3-yl)octanoic acid ethyl ester (104 g wet solid was obtained from 35 g of 1,3-Benzoxazine-2,4-dione) at ambient temperature followed by addition of sodium borohydride (0.7 g) and stirred for 30 minutes. The aqueous sodium hydroxide solution (36.75 g NaOH in 147 mL water) was charged into reaction mass and stirred at 95° C. for 120 minutes. The reaction mixture was cooled to 0-5° C. followed by pH adjustment between 9 and 10 using concentrated HCl (26 mL). The reaction mixture was brought to ambient temperature and aqueous layer was washed using toluene (175 mL×3), wherein toluene layer was discarded. Charge sodium borohydride (0.7 g) into the reaction mixture and stir for 60 min at ambient temperature. The reaction mixture was charged into pre-cooled mixture of HCl (79 mL conc. HCl in 210 mL water) and stirred for 30 minutes at 0-5° C. The solid was filtered, washed with water (70 mL). The wet solid was subjected to slurry wash with water (175 mL) for 1 hour followed by filtration and washing with water (245 mL) followed by suck-drying. The wet Salcaprozic Acid solid, free from colored impurity was further purified as described in Step 3 below.

Step 3: Purification of Salcaprozic Acid

The wet Salcaprozic Acid obtained above in Method B was charged with acetone (50 mL) and stirred for about 5 hours at ambient temperature. The reaction mixture was then charged with water (100 mL) and further stirred for about an hour at ambient temperature. The solid was filtered, washed with a mixture of acetone:water (10 mL:20 mL) and suck-dried for 2 hours. The wet cake was unloaded and dried under vacuum at 50-55° C. for 12 hours to obtain pure Salcaprozic Acid (12.9 g).

The wet Salcaprozic Acid obtained above in Method C was charged acetone (125 mL) and stirred for about 5 hours at ambient temperature. The reaction mixture was then charged with water (250 mL) and further stirred for about an hour at ambient temperature. The solid was filtered, washed with a mixture of acetone:water (25 mL:50 mL) and suck-dried for 2 hours. The wet cake was unloaded and dried under vacuum at 50-55° C. for 12 hours to obtain pure Salcaprozic Acid (28.5 g).

The wet Salcaprozic Acid obtained above in Method D was charged in acetone (50 mL) and stirred for about 5 hours at ambient temperature. The reaction mixture was then charged with water (100 mL) and further stirred for about an hour at ambient temperature. The solid was filtered, washed with a mixture of acetone:water (10 mL:20 mL) and suck-dried for 2 hours. The wet cake was unloaded and dried under vacuum at 50-55° C. for 12 hours to obtain pure Salcaprozic Acid (13.5 g).

The wet Salcaprozic Acid obtained above in Method E was charged acetone (50 mL) and stirred for about 5 hours at ambient temperature. The reaction mixture was then charged water (100 mL) and further stirred for about an hour at ambient temperature. The solid was filtered, washed with a mixture of acetone:water (10 mL:20 mL) and suck-dried for 2 hours. The wet cake was unloaded and dried under vacuum at 50-55° C. for 12 hours to obtain pure Salcaprozic Acid (13.0 g).

The wet Salcaprozic Acid obtained above in Method F was charged acetone (50 mL) and stirred for about 5 hours at ambient temperature. The reaction mixture was then charged water (100 mL) and further stirred for about an hour at ambient temperature. The solid was filtered, washed with a mixture of acetone:water (10 mL:20 mL) and suck-dried for 2 hours. The wet cake was unloaded and dried under vacuum at 50-55° C. for 12 hours to obtain pure Salcaprozic Acid (12.7 g).

The wet Salcaprozic Acid obtained above in Method G was charged acetone (175 mL) and stirred for about 5 hours at ambient temperature. The reaction mixture was then charged water (350 mL) and further stirred for about an hour at ambient temperature. The solid was filtered, washed with a mixture of acetone:water (35 mL:70 mL) and suck-dried for 2 hours. The wet cake was unloaded and dried under vacuum at 50-55° C. for 12 hours to obtain pure Salcaprozic Acid (47.03 g).

Example 3: Preparation of Sodium Salt of Salcaprozic Acid (SNAC)

An aqueous sodium hydroxide solution (15.04 g NaOH in 35 mL water) was slowly added to a solution of Purified Salcaprozic Acid (100 g) (Purified Salcaprozic Acid obtained as in Example-1: Method-A2, Step-4) in ethanol (300 mL), and stirred for 20 minutes below 35° C. Reaction mixture was diluted by addition of ethanol (300 mL) and further stirred for 30 minutes. Heptane (360 mL) was added as anti-solvent and stirred for 30 minutes at 10-15° C. The resulting reaction mixture was filtered and solid was washed with heptane (2×100 mL). The resulting sodium salt of Salcaprozic Acid (87 g) (SNAC) was dried under vacuum at 60-65° C. for 12-15 hours. HPLC Purity: 99.92%, Absorbance (at 400 nm): 0.01 and % of Transmittance: 99.42.

Example 4: Comparative Preparation of Salcaprozic Acid without Using Additional Reagents for Removing Colored Impurity Water (50 mL) was charged to 8-(2,4-dioxo-1,3-benzoxazin-3-yl)octanoic acid ethyl ester (118.88 g wet solid was obtained from 40 g of 1,3-Benzoxazine-2,4-dione using the process of Example 1, Step 1) at ambient temperature and stirred for 30 minutes. The reaction mixture was charged into sodium hydroxide solution (42 g NaOH in 168 mL water) and stirred at 95° C. for 120 minutes. The reaction mixture was cooled to 0-5° C. followed by pH adjustment between 9 and 10 using concentrated HCl (30 mL). The reaction mixture was brought to ambient temperature and aqueous layer was washed using toluene (200 mL×3), wherein toluene layer was discarded. The reaction mixture was charged into pre-cooled mixture of HCl (90 mL conc. HCl in 240 mL water) and stirred for 30 minutes at 0-5° C. The solid was filtered, washed with water (80 mL). The wet solid was subjected to slurry wash with water (200 mL) for 1 hour followed by filtration and washing with water (280 mL) followed by suck-drying. Weight of the wet cake of colored Salcaprozic Acid was 96 g.

Example 5: Purification/Reprocess of Colored Salcaprozic Acid (Obtained from Example 4) Using 2% Sodium Borohydride/Hydrazine/Benzotriazole of 1,3-Benzoxazine 2,4-Dione Wet Salcaprozic Acid (24 g wet solid made by process of Example 4 from 10 g of 1,3-Benzoxazine-2,4-dione) was charged into Sodium hydroxide solution (5 g Sodium hydroxide in 50 mL water) and stirred for 10 to 15 minutes at ambient temperature. The reaction mixture was treated with hydrazine, sodium borohydride, or benzotriazole (0.2 g) and further stirred for about 60 to 70 minutes at ambient temperature. The reaction mass was cooled to 10° C. to 15° C. The solid was isolated by addition of dilute hydrochloric acid solution. The solid was filtered, washed water (10 mL). The wet solid was subjected to slurry wash with water (50 mL) for 1 hour followed by filtration and washing with water (20 mL) followed by suck-drying. The wet cake was unloaded and dried under vacuum at 50-55° C. for 12 hours to obtain pure colorless Salcaprozic Acid.

Example 6: Preparation of Potassium Salt of Salcaprozic Acid

Salcaprozic Acid (100 g) was charged to a solution of potassium hydroxide (1.1 eq; 22.09 g) in ethanol (266 mL) at 60-65° C. The reaction temperature was maintained for 1 hour followed by hot filtration through 0.2 micron. The reaction mixture was cooled to 25-30° C. Diisopropylether (2857 mL) was added to the reaction mixture followed by stirring for 60-90 minutes at 25-35° C. The resulting reaction mixture was filtered and potassium salt of Salcaprozic Acid was washed with diisopropylether (2×200 mL). The solid was dried under vacuum at 60-65° C. for 24 hours to obtain potassium salt of Salcaprozic Acid (90 g).

Example 7: Comparative Data

Absorbance and Transmittance of 1% solution of sodium salt of Salcaprozic Acid was checked at 400 nm and 600 nm respectively using UV-Vis Spectrophotometer (Perkin Elmer Lambda 365), the absorbance, transmittance and purity of the sodium salt of Salcaprozic Acid prepared according to various methods is shown in Table 1.

TABLE 1

| Color and Clarity Data for Sodium Salt of Salcaprozic Acid | | | | HPLC Purity data of Salcaprozic Acid | |
|---|---|---|---|---|---|
| Process/ Reference | Experiment details | Absorbance (at 400 nm) | % of Transmission | Purity (%) | Single maximum impurity (%) |
| Prior art process from EP2604175B1 | Prior art process using EDTA | 0.023 | 98.39 | 99.73 | 0.17 |
| Original Process without any treatment | Example-4: Experiment performed without any treatment | 0.38 | 94.82 | — | — |
| Developed process of present invention after Purification Step | Method A-1: using benzotriazole (2%) and Sodium borohydride (2%) | 0.01 | 99.34 | 99.88 | 0.04 |
| | Method A-2: using benzotriazole (2%) | 0.01 | 99.42 | 99.88 | 0.05 |
| | Method-B: using benzotriazole (5%) | 0.01 | 99.19 | 99.89 | 0.07 |
| | Method-C: using benzotriazole (1%) | 0.01 | 99.30 | 99.89 | 0.06 |
| | Method-D: using hydrazine (1%) | 0.01 | 99.31 | 99.94 | 0.02 |
| | Method-E: using hydrazine (2%) | 0.01 | 99.38 | 99.93 | 0.03 |
| | Method-F: using hydrazine (5%) | 0.01 | 99.63 | 99.92 | 0.03 |
| | Method-G: using sodium borohydride (4%) | 0.01 | 99.30 | 99.92 | 0.05 |

From above data, it is evident that the process of present invention of using novel reagents benzotriazole, hydrazine and sodium borohydride gives better results as compared to prior art process. Also, as per example 4, if any reagent is not used in the process, it leads to Salcaprozic Acid with greater absorbance.

While the present invention has been described with reference to particular embodiments and arrangements of parts, features, and the like, it is not limited to these embodiments or arrangements. Indeed, modifications and variations will be ascertainable to those of skill in the art, all of which are inferentially and inherently included in these teachings.

What is claimed is:

1. A process for the preparation of Salcaprozic Acid or a pharmaceutically acceptable salt thereof, comprising:
   a. hydrolyzing a compound of formula II:

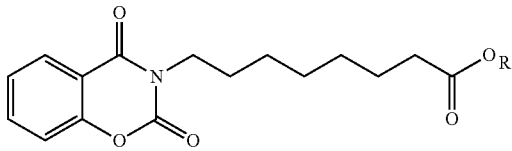

formula II wherein, R is straight or branched chain alkyl in the presence of benzotriazole, hydrazine, sodium borohydride or mixture thereof; and
   b. isolating Salcaprozic Acid, which is free from colored impurity.

2. The process of claim 1, wherein the compound of formula II is prepared from 1,3-Benzoxazine-2,4-dione and the compound of formula II is hydrolyzed in presence of about 0.1% to about 10% by weight of the benzotriazole, hydrazine, sodium borohydride or mixture thereof relative to weight of the 1,3-Benzoxazine-2,4-dione.

3. The process of claim 2, wherein about 1% to about 5% by weight of the benzotriazole, hydrazine, sodium borohydride or mixture thereof is used relative to weight of the 1,3-Benzoxazine-2,4-dione.

4. The process of claim 1, wherein the step of hydrolyzing in the presence of benzotriazole, hydrazine, sodium borohydride or mixture thereof occurs at ambient temperature.

5. The process of claim 2, wherein the step of hydrolyzing comprises adding aqueous metal hydroxide and stirring at an elevated temperature up to about 95° C.

6. The process of claim 5, further comprising cooling to 0-5° C. followed by adjusting pH to about 9 to about 10.

7. The process of claim 6, further comprising washing the pH adjusted solution with an organic solvent followed by discarding the organic washing solvent.

8. The process of claim 7, wherein the step of isolating comprises lowering pH of the washed solution to obtain a wet solid Salcaprozic Acid.

9. The process of claim 1, further comprising filtering and washing the isolated Salcaprozic Acid with a mixture of acetone and water.

10. The process of claim 1, further comprising contacting Salcaprozic Acid, which is free from colored impurity, with an organic or inorganic base in an organic solvent, water, or a mixture thereof to obtain a salt of Salcaprozic Acid.

11. The process of claim 10, wherein absorbance at 400 nm of a 1% solution of the salt of Salcaprozic Acid is less than 0.03.

12. The process of claim 10, wherein transmission at 600 nm of a 1% solution of the salt of Salcaprozic Acid is greater than 95%.

13. A process for removing a colored impurity from a Salcaprozic Acid salt comprising treating a solution of the salt with benzotriazole, hydrazine, sodium borohydride or a mixture thereof.

14. The process of claim 13, wherein absorbance at 400 nm of a 1% solution of the treated salt is less than 0.03.

15. A process for the preparation of Salcaprozic Acid or a pharmaceutically acceptable salt thereof, comprising:
   a. preparing 8-(2,4-dioxo-1,3-benzoxazin-3-yl)octanoic acid ethyl ester using 1,3-Benzoxazine-2,4-dione;
   b. contacting the 8-(2,4-dioxo-1,3-benzoxazin-3-yl)octanoic acid ethyl ester with about 1% to about 5% by weight of benzotriazole, hydrazine, Sodium borohydride or mixture thereof relative to the amount of 1,3-Benzoxazine-2,4-dione,
   c. adding aqueous metal hydroxide and stirring at an elevated temperature up to about 95° C.;
   d. cooling to 0-5° C. followed by adjusting pH to about 9 to about 10;
   e. washing the pH adjusted solution with an organic solvent to remove byproducts and impurities; and
   f. lowering pH of the washed solution to isolate a wet solid Salcaprozic Acid.

16. The process of claim 15, wherein the step of contacting occurs at ambient temperature.

17. The process of claim 15, further comprising
   g. filtering and washing the wet solid Salcaprozic Acid with a mixture of acetone and water to obtain purified Salcaprozic Acid.

18. The process of claim 17, wherein an amount of any single impurity in the purified Salcaprozic Acid is less than 0.1%.

19. The process of claim 15, wherein the Salcaprozic Acid is free of colored impurity.

20. The process of claim 15, wherein 1% solution of a sodium salt of the wet Salcaprozic Acid has absorbance at 400 nm of less than 0.02 or transmission at 600 nm of greater than 99%.

* * * * *